(12) United States Patent
Pettit

(10) Patent No.: US 6,451,986 B1
(45) Date of Patent: *Sep. 17, 2002

(54) SITE SPECIFIC PROTEIN MODIFICATION

(75) Inventor: Dean K. Pettit, Seattle, WA (US)

(73) Assignee: Immunex Corporation, Seattle, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,530

(22) Filed: Jun. 22, 1998

(51) Int. Cl.$^7$ .......................... C07K 1/00; C07H 21/04; C12N 1/00; C12P 21/06; G01N 33/566
(52) U.S. Cl. ...................... 530/402; 530/300; 530/350; 435/7.1; 435/7.6; 435/7.21; 435/69.1; 435/69.5; 435/252.3; 436/501; 536/23.5; 536/23.52; 514/2
(58) Field of Search .............................. 530/402, 350; 435/69.1, 7.1, 7.6, 7.21, 69.5, 252.3; 536/23.5, 23.52; 436/501; 514/2

(56) References Cited

U.S. PATENT DOCUMENTS

| | | | |
|---|---|---|---|
| 4,179,337 A | 12/1979 | Davis et al. | |
| 4,904,584 A | 2/1990 | Shaw | 435/69.4 |
| 5,235,028 A | 8/1993 | Barany et al. | |
| 5,514,572 A | 5/1996 | Veronese et al. | |
| 5,776,895 A | * 7/1998 | Alber et al. | 514/12 |

FOREIGN PATENT DOCUMENTS

| | | |
|---|---|---|
| WO | WO 98 05824 A | 6/1989 |
| WO | WO 94/13322 | 6/1994 |
| WO | WO 94/20069 | 9/1994 |
| WO | WO 96/11213 | 4/1996 |
| WO | WO 97 11178 A | 3/1997 |
| WO | WO 98 35026 A | 8/1998 |

OTHER PUBLICATIONS

Wang, Q–C., et al., Cancer Research 53(4588–4594), Oct. 1993.*
Banner, D.W. et al., Cell 73(431–445) May, 1993.*
Mohler, K.M., et al., J. Immunology 151:3(1548–1561), Aug. 1993.*
Banner, D.W. et al. Crystal Structure of the soluble human 55 kd TNF receptor–human TNF–beta complex: implications for TNF receptor activation. Cell 73(431–445), May 1993.*
Benhar, I. et al. Mutations of two Lysine residues in the CDR loops of a recombinant immunotoxin that reduce its sensistivity to chemical derivatization. Bioconjugate Chem. 5(321–326), Jan. 1994.*

Mohler et al., "Soluble Tumor Necrosis Factor (TNF) Receptors are Effective Therapeutic Agents in Lethal Endotoxemia and Function Simultaneously as Both TNF Carriers and TNF Antagonists", *The Journal of Immunology* 151:548–1561, 1993.

Onozaki et al., "Human Interleukin 1 is a Cytocidal Factor for Several Tumor Cell Lines", *The Journal of Immunology* 135:3962–68, Dec. 1985.

Sartore et al., "Accurate Evaluation Method of the Polymer Content in Monomethoxy (Polyethylene Glycol) Modified Proteins Based on Amino Acid Analysis", *Applied Biochemistry and Biotechnology* 31:213–222, 1991.

Goodson et al., "Site–Directed Pegylation of Recombinant Interleukin–2 at its Glycosylation Site", *Bio/Technology* 8:343–46, Apr. 1990.

Kinstler et al., "Characterization and Stability of N–terminally PEGylated rhG–CSF", *Pharmaceutical Research* 13:996–1002, 1996.

Pettit et al., "Site Protected PEGyolation of Recombinant (p75) Tumor Necrosis Factor Receptor," *Division of Polymer Chemistry, Inc. American Chemical Society* 38:1, 574–575, Apr. 1997.

Felix, Arthur M., "Site–Specific Poly(ethylene glycol)ylation of Peptides," *ACS Symposium Series* 680:ch 16, 218–239, 1997.

Banner et al., "Crystal Structure of the Soluble Human 55 kd TNF Receptor–Human TNFβComplex: Implications for TNF Receptor Activation," *Cell*, 73:431–445, May 7, 1993.

Hershfield et al., "Use of site–directed mutagenesis to enhance the epitope–shielding effect of covalent modification of proteins with polyethylene glycol," *Proc. Natl. Acad. Sci. USA*, 88:7185–7189, Aug. 1991.

Delgado et al., "The Uses and Properties of PEG–Linked Proteins", *Critical Reviews in Therapeutic Drug Carrier Systems* 9:249–304, 1992.

(List continued on next page.)

Primary Examiner—Yvonne Eyler
Assistant Examiner—Michael T Brannock
(74) Attorney, Agent, or Firm—Janis C. Henry

(57) ABSTRACT

Processes for conjugating proteins with polyethylene glycol are disclosed. The disclosed processes provide modified proteins having little or no decrease in their activity and include the steps of deleting at least one amino acid residue on the protein, replacing the at least one amino acid residue with an amino acid residue that does not react with polyethylene glycol, and contacting the protein with polyethylene glycol under conditions sufficient to conjugate the polyethylene glycol to the protein. This advantageous retention of a desired protein activity is attributed to the availability of one or more protein binding sites which is unaltered in the conjugation process and thus remains free to interact with a binding partner ligand or cognate subsequent to the conjugation process.

10 Claims, 1 Drawing Sheet

OTHER PUBLICATIONS

Urrutigoity et al., "Biocatalysis in Organic Solvents with a Polymer–Bound Horseradish Peroxidase", *Biocatalysis* 2:145–149, 1989.

Pettit et al., "Structure–Function Studies of Interleukin 15 using Site–specific Mutagenesis, Polyethlene Glycol Conjugation, and Homology Modeling", *The Journal of Biological Chemistry* 272:2312–2318, 1997.

Gombotz et al., "Biodegradable Polymers for Protein and Peptide Drug Delivery", *Bioconjugate Chemistry* 6:332–351, 1995.

Lu, Yi–An and Felix, Arthur M., Pegylated peptides II, *Int. J. Peptide Protein Res.* 43:127–138, 1994.

Zalipsky, S., "Chemistry of polyethylene glycol conjugates with biologically active molecules," *Advanced Drug Delivery Reviews*, 16:157–182, 1995, XP002037428.

Hershfield, M. S. et al., "Use of site–directed mutagenesis to enhance the epitope–shielding effect of covalent modification of proteins with polyethylene glycol," *Proc. Natl. Acad. Sci. of USA*, 88:7185–7189, Aug. 1991, XP002097495.

* cited by examiner

```
  1 L P A Q V A F T P Y   11 A P E P G S T C R L   21 R E Y Y D Q T A Q M   31 C C S K C S P G Q H   41 A K V F C T K T S D
 51 T V C D S C E D S T   61 Y T Q L W N W V P E   71 C L S C G S R C S S   81 D Q V E T Q A C T R   91 E Q N R I C T C R P
101 G W Y C A L S K Q E  111 G C R L C A P L R K  121 C R P G F G V A R P  131 G T E T S D V V C K  141 P C A P G T F S N T
151 T S S T D I C R P H  161 Q I C N V V A I P G  171 N A S M D A V C T S  181 T S P T R S M A P G  191 A V H L P V S T R S
201 Q H T Q P T P E P S  211 T A P S T S F L L P  221 M G P S P P A E G S  231 T G D
```

☐ = POTENTIAL RESIDUES FOR PEG CONJUGATION

⌐ ¬ = RESIDUES WHICH MAKE CONTACT WITH TNFα

SITE SPECIFIC PROTEIN MODIFICATION

BACKGROUND OF THE INVENTION

1. Field of the Invention

The present invention relates to processes for modifying proteins. More particularly, the present invention involves processes for linking polyethylene glycol to proteins in a manner which provides advantages associated with polyethylene glycol conjugated proteins while maintaining a desired protein bioactivity.

2. Description of Related Art

Processes and reagents for chemically modifying proteins have been used extensively for decades. Traditionally, protein chemical modifications were carried out in order to study their functional properties and structural characteristics. With the emergence of recombinant DNA techniques and interest in protein therapeutics, researchers have chemically modified proteins to improve their clinical performance. In particular, processes for conjugating proteins with polyethylene glycol have gained widespread use within the pharmaceutical and biochemical communities as a result of numerous improved pharmacological and biological properties associated with polyethylene glycol conjugated proteins. For example, polyethylene glycol conjugated proteins are known to have significantly enhanced plasma half life, and thus have substantially improved the clinical usefulness. Additionally, polyethylene glycol conjugated proteins generally have reduced antigenicity and immunogenicity, thereby are less prone to causing life-threatening anaphylaxis.

Another benefit associated with polyethylene glycol conjugated proteins is that of water solubility which is increased as a result of the high water solubility of polyethylene glycol. The increased water solubility can improve the protein's formulation characteristics at physiological pH's and can decrease complications associated with aggregation of low solubility proteins.

Additionally, polyethylene glycol conjugated proteins have found use in bioindustrial applications such as enzyme based reactions in which the reaction environment is not optimal for the enzyme's activity. For example, some polyethylene glycol conjugated enzymes demonstrate a wider optimum pH activity and reduced optimum activity temperature. Moreover, enzymes having reduced activity in many organic solvents have been successfully conjugated with polyethylene glycol to a degree that renders them useful for catalyzing reactions in organic solvents. For example, polyethylene glycol has been conjugated with horseradish peroxidase which then becomes soluble and active in chloroform and toluene (Urrotigoity et al., *Biocatalysis*, 2:145–149, 1989).

Polyethylene glycol conjugated proteins vary in the extent to which plasma circulation half life is increased, immunogenicity is reduced, water solubility is enhanced, and enzymatic activity is improved. Factors responsible for these variations are numerous and include the degree to which the protein is substituted with polyethylene glycol, the chemistries used to attach the polyethylene glycol to the protein, and the locations of the polyethylene glycol sites on the protein.

The most common methods for attaching polyethylene glycol to proteins involve activating at least one of the hydroxyl groups on the polyethylene glycol with a functionality susceptible to nucleophilic attack by the nitrogen of amino groups on the protein. These methods generally result in loss of biological activity due to the nonspecific attachment of polyethylene glycol.

Alternative approaches to conjugating proteins with polyethylene glycol include controlling the conjugation reactants and conditions so that the conjugation site is confined to the N-terminus (Kinstler et al. *Pharm. Res.* 13:996, 1996); attaching polyethylene glycol to protein carbohydrate functionalities (Urrutigoity et al. *Biocatalysis* 2:145, 1989); attaching polyethylene glycol at protein cysteine residues (Goodson et al. *Biotechnology* 8:343, 1990); attaching polyethylene glycol during solid phase and solution phase peptide synthesis (Felix, *ACS Symposium Series* 680 ch 16, 1997) and, selectively replacing protein arginine residues with lysine residues that provide an polyethylene glycol attachment site (Hershfield et al. *Proc. Natl. Acad. Sci.* 88:7185, 1991). While these offer some degree of control of the reaction site, there is a continuing need for improved methods for providing polyethylene glycol conjugated proteins. In particular, it would be desirable to provide methods for conjugating proteins with polyethylene glycol that result in modified proteins having enhanced bioactivity or little loss in bioactivity while maintaining the benefits of polyethylene glycol conjugation, including substantially decreased immunogenicity, increased solubility, and prolonged circulation half lives characteristic of modified proteins.

SUMMARY OF THE INVENTION

The present invention provides protein modification processes that result in modified proteins having little or no decrease in an activity associated with the protein. More particularly, the invention described herein includes processes for modifying a protein by first deleting one or more amino acid sites on the protein that is suitable for polyethylene glycol conjugation and then contacting the protein with polyethylene glycol under conditions suitable for conjugating the polyethylene glycol to the protein. Preferably, the deleted amino acid residue is replaced with an amino acid residue that does not react with polyethylene glycol. The resulting polyethylene glycol conjugated protein has improved characteristics over proteins modified according to prior art procedures. An advantageous retention of activity is attributed to the availability of one or more protein binding sites which is unaltered in the protein modification process and thus remains free to interact with a binding partner subsequent to the modification process. Within the present invention are proteins useful for polyethylene glycol conjugation and polyethylene glycol conjugated proteins prepared by processes described herein.

BRIEF DESCRIPTION OF THE DRAWINGS

FIG. 1 illustrates lysine residues within p75 TNF receptor extracellular domain that are polyethylene glycol conjugation sites and lysine residues that make contact with TNFα.

DETAILED DESCRIPTION OF THE INVENTION

The present invention provides processes and reagents for conjugating proteins or polypeptides with polyethylene glycol in a manner that results in polyethylene glycol conjugated proteins having little or no reduction in a desired activity. More specifically, the present invention provides processes for conjugating polyethylene glycol with proteins under conditions which preclude polyethylene glycol conjugation at one or more selected sites on the protein. When the one or more selected sites is active in a protein binding domain, preventing polyethylene glycol conjugation at the site in accordance with the present invention contributes to maintaining a desired bioactivity while providing benefits associated with polyethylene glycol conjugation.

The processes of the present invention are based upon the discovery that by deleting one or more selected amino acid residues that are capable of reacting with polyethylene glycol sites, and then conjugating the protein with polyethylene glycol, the resulting polyethylene glycol modified protein does not demonstrate a significant reduction in a desired activity. In one embodiment, the selected amino acid residue is a lysine residue that, if reacted with a polyethylene glycol, interferes with the ability of the resulting conjugated protein to bind with its binding partner, substrate, or receptor. It is believed that the selected amino acid residues are associated with binding sites, and, if modified, interfere with the conjugated protein's structural elements that determine protein conformation and function. By deleting the selected amino acid residue, polyethylene glycol does not modify the protein at the site of the selected amino acid residue during a subsequent polyethylene glycol modification reaction. Preferably, in order to preserve the number of amino acid residues and maintain the optimum protein conformation, the deleted amino acid residue is replaced with an amino acid residue that is not reactive with polyethylene glycol under the reaction conditions. For example, lysine can be deleted and replaced with an arginine residue. Arginine has the same structure as lysine, with the exception of the polyethylene glycol reactive $\epsilon$-NH$_2$ functionality on lysine which is absent in arginine.

Any protein is suitable for polyethylene glycol modification in accordance with the present invention including but not limited to protein ligands, receptors, antigens, antibodies, enzymes, protein fragments, peptides, and polypeptides. Particularly desirable protein candidates for polyethylene glycol modification as described herein are those which, subsequent to their modification by prior art methods, demonstrate a reduction in a desired activity. Other proteins which are suitable for modification in accordance with the present invention are those having multiple binding sites. In this embodiment, a protein may be conjugated with polyethylene glycol so that an activity associated with one or more of the multiple binding sites can be reduced while maintaining an activity associated with one or more different binding sites. This is accomplished by deleting one or more selected amino acid residues that are associated with binding sites for which activity is to be maintained and which are capable of reacting with polyethylene glycol, and leaving amino acid residues associated with binding sites for which activity is to be reduced for subsequent polyethylene glycol conjugation. Preferably, the deleted amino acid residue or residues is replaced with an amino acid residue that is not reactive with polyethylene glycol under the reaction conditions. Additionally, the deleted amino acid residue or residues is replaced with an amino acid residue that does not significantly diminish the activity of the native protein. The resulting polyethylene glycol conjugated protein will have an activity associated with selected binding sites and, depending upon the degree to which additional sites are involved in the conjugation process, will have a diminished, or no activity, associated with such additional sites. This approach is useful in cases in which cognate or substrate binding to one or more protein binding sites is desirably suppressed in certain clinical, diagnostic or industrial applications.

Proteins that may be modified in accordance with the present invention include those having utility in clinical and diagnostics applications and those used in the biotechnology industry, such as enzymes in bioreactors. Receptors which may be modified as taught herein include cytokine receptors, for example, TNFR, IL-4R, IL-1R, IL-17R, IL-15R, p55 TNFR:Fc and p75 TNFR:Fc. Candidate antibodies for conjugation include but are not limited to OKT3 (anti-T-Cell), AVAKINE™ (anti-TNF) and anti Her2/Neu. Enzymes of interest for conjugation include CD39, tPA, and DNAse. Many proteins have multimeric binding sites and require more than one association for activity. Such proteins are particularly desirable for modification since loss of one binding site leaves the whole protein inactive. Members of the group of multimeric proteins include TNF, hGH, CD40L, and FasL. Other candidate protein ligands are known to bind multiple receptor subunits and include IL-2, IL-15, GM-CSF, and G-CSF.

In accordance with the present invention, a selected amino acid residue is one that is associated with a site on a protein which contributes to a specific function of that protein, and which is reactive with polyethylene glycol under the protein modification reaction conditions. The selected amino acid residue may be directly involved with a binding association with a protein binding partner. Alternatively, the amino acid may be sufficiently central to the spatial configuration of the protein that modifying the protein with polyethylene glycol results in a significant loss of desirable properties even though the amino acid residue is neither within a binding site nor directly or physical involved with the protein's interaction with a binding partner. Sites include, but are not limited to, cognate sites or substrate binding sites which are associated with a protein activity. Amino acid residues that are reactive with polyethylene glycol under conditions known in the art include those having residues having nucleophilic moieties that are available for reaction with polyethylene glycol or an activated polyethylene glycol. For example, lysine is reactive with polyethylene glycol through its $\epsilon$-$NH_2$; aspartic acid and glutamic acid are reactive with polyethylene glycol through their COOH (carboxyl) functionalities; serine and threonine are potentially reactive through their OH (hydroxyl) sites; and, cysteine with available SH (sulfhydryl) groups may also react with polyethylene glycol. Conditions suitable for reactions between polyethylene glycol or activated polyethylene glycols and specific amino acid residues in proteins are known and those skilled in the art are charged with knowledge such reactions. It is known in the art that lysine residues react with activated polyethylene glycol under favorable reaction conditions and with minimum side reactions. Thus, in accordance with the present invention, lysine residues are typically the targeted residue and the reaction conditions are controlled to maximize the reaction between polyethylene glycol and lysine.

Determining a suitable amino acid residue to select for deletion and, preferably, replacement, can be accomplished using a number of different techniques. In cases where the three dimensional structure and epitopes or structural elements that determine protein function are not known, one method involves using site directed mutagenesis techniques to empirically determine amino acid residues that are associated with a site on a protein which contribute to a specific function of that protein. More particularly, one or more predetermined polyethylene glycol reactive amino acid residues on the protein can be deleted and preferably replaced with non reactive amino acid residues using mutagenesis and recombinant DNA methodologies. Conjugating the thus modified protein with polyethylene glycol and then testing the resulting polyethylene glycol conjugated protein for activity and other relevant properties provides valuable information relating to the suitability of the predetermined amino acid residue or residues for deletion and replacement. Sequentially repeating the above described process for different polyethylene glycol reactive amino acid residues will provide more complete information relating to the role of the deleted amino acid residue in determining the function and activity of the protein. For example, if a protein has 8 lysine residues, DNA encoding the protein can be mutated in a site directed manner to produce a number of different mutants with one or more of the codons coding for the lysine residues replaced with codons coding for an arginine residue. The specific lysine coding codons that are mutated can include one selected codon, all of the lysine coding codons, are any permutation of the lysine coding codons, including the simultaneous mutagenesis of DNA coding lysine residues that are adjacent to each other.

After expressing, collecting and purifying the engineered proteins encoded by the mutated DNA, the expressed proteins can be reacted with polyethylene glycol to form a conjugated protein. Then the conjugated protein can be tested for functional activity and other characteristics such as immunogenicity, physiological clearance, and solubility. The polyethylene glycol conjugated proteins that have the desired activity and most favorable clearance, solubility and immunogenicity properties also contain the desired selected lysine residues i.e., the residues that had been deleted and replaced prior to reacting the protein with polyethylene glycol.

For many proteins, the location of polyethylene glycol reactive amino acid residues and their conformational contribution to the structure and function of the protein are known. Among these proteins, are those for which the crystalline structure of the protein is known, and, in some cases, the crystalline structure of the protein-binding partner complex is known. For these proteins, determining a selected amino acid residue typically requires only identifying the residues that are within the protein's binding domain or in close spatial proximity to the protein's binding region and identifying those residues that are reactive with polyethylene glycol under the contemplated polyethylene glycol reaction conditions.

In accordance with the present invention, deleting a selected amino acid residue on the protein can be accomplished with a variety of suitable procedures that provide modified proteins. In the context of the present invention, such procedures include, but are not limited to, site directed mutagenesis techniques and direct protein synthesis methods in which the protein lacking one or more selected amino acid residues is synthesized using standard protein synthesis procedures known in the art. As noted above, preferably the process of deleting a selected amino acid residue additionally involves replacing the selected amino acid residue with an amino acid residue that is not reactive with polyethylene glycol.

Proteins may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein.

Alterations of amino acid sequence, including deleting selected amino acid residues and replacing the deleted residues with a different residue, may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

Similarly, the present invention provides methodologies for preventing multimeric association of proteins. For example, polyethylene glycol can be selectively conjugated onto sites in or around the multimeric association interface, while preserving the binding of the protein for its natural cognate through "site protected" polyethylene glycol conjugation as taught herein, thus preventing receptor multimerization.

After preparing an altered protein having at least one selected amino acid residue that is deleted and preferably replaced with an amino acid residue that does not react with polyethylene glycol under the chosen reaction conditions, the altered protein is conjugated with polyethylene glycol. Reagents and procedures for forming polyethylene glycol-protein conjugates are known in the art per se and are generally applicable to the practice of the present invention. Typically, these procedures involve first providing an activated polyethylene glycol in which one or both hydroxyl groups on a polyethylene glycol are activated, and reacting the activated polyethylene glycol with active sites on a protein selected for polyethylene glycol conjugation. As mentioned above, the most widely utilized procedures for conjugating a protein with polyethylene glycol are based upon a nucleophilic reaction between protein amino sites (the ε-amine nitrogen of lysine or the α-amino terminal amine) and an activated hydroxyl of polyethylene glycol. Since sulfhydryls are also nucleophiles, cysteine sulfhydryls that are not part of a disulfide bridge are also potential reaction sites on the protein. The general principles of polyethylene glycol conjugation with proteins, and common activating reagents are described by Delgado et al. in The Uses and Properties of PEG-Linked Proteins, from *Critical Reviews in Therapeutic Drug Carrier Systems*, 9(3,4):249–304 (1992) and the ACS Symposium Series 680 ed. y Harris et al., *Poly(ethylene glycol) Chemistry and Biological Applications* 1997, both of which are incorporated herein by reference.

Activated forms of polyethylene glycol and monomethoxypolyethylene glycol are commercially available and may be used in processes of the present invention. Most notably, Shearwater Polymers, Inc of Huntsville, Ala. provides a number of polyethylene glycol polymers and polyethylene glycol derivatives. The Shearwater Polymers, Inc Catalog (Shearwater Polymers, Inc. Catalog Functionalized Biocompatible Polymers for Research, 1997–1998 incorporated herein by reference) describes and makes available a wide variety of activated polyethylene glycols suitable for coupling with proteins under a wide range of reaction conditions. This catalog additionally provides preferred reaction conditions for their derivatized polyethylene glycol reagents. Those skilled in the art having been made aware of the numerous reagents suitable for conjugating proteins with polyethylene glycol will appreciate the variety of reagent choices in view of the nature of the protein selected, the nature of the reactive amino groups or sulfhydryl groups on the protein and the end use of the conjugated protein. For example, to provide conjugated proteins having improved solubility, activity characteristics and delivery properties but not necessarily increased clinical clearance time, a succinirmidyl succinate activated polyethylene glycol (SS-PEG) can be used in the conjugation reaction. The ester link to the protein is less stable and will hydrolyze in vivo, releasing the polyethylene glycol from the protein. Activated polyethylene glycols are available which will more preferentially react with amino groups as opposed to sulfhydryl groups and vice versa. Commonly selected activated polyethylene glycols include succinimidyl carbonate activated polyethylene glycols, succinimidyl succinate activated polyethylene glycol and succinimidyl propionic acid polyethylene glycols.

As an alternative to selecting commercially available activated polyethylene glycols, a polyethylene glycol of interest may be activated using reagents which react with hydroxyl functionalities to form a site reactive with a site on a protein of interest. Typically, the protein reactive site is an amino group but can be a sulfhydryl or hydroxyl and the activated polyethylene glycol typically is an active ester or imidizole (See pgs 274– 285 ibid.) Preferably, only one hydroxyl functionality of the polyethylene glycol is activated which can be accomplished by utilizing a monomethoxypolyethylene glycol in an activating reaction. However, processes in which two hydroxyls are activated are within the scope of the present invention. Depending upon the nature of the activating group and the nucleophilic attack, the activating moiety may or may not become incorporated into the protein following the nucleophilic reaction.

The polyethylene glycol may be of any molecular weight but is preferably in the range of about 500 to about 100,000 and more preferably in the range of 2,000 to 20,000. The criteria for selecting a specific polyethylene glycol molecular weight include, but are not limited to, the molecular weight of the protein selected for modification, the charge on the protein, type of protein and the number and location of potential sites for conjugation. Immunological and plasma half-life characteristics of proteins conjugated with different molecular polyethylene glycols molecular weight are discussed in Delgado et al, *Critical Reviews in Therapeutic Drug Carrier Systems*, 9: 249, 1992 and the ACS Symposium Series 680, Harris et al. *Poly(ethylene glycol) Chemistry and Biological Applications*, 1997. As known in the art, in general, the greater the amount of polyethylene glycol conjugated to the protein, the longer the plasma half-life and the greater the protein solubility. Since the molecular weight cut-off for glomerular filtration is roughly 70 kDa, proteins having molecular weights less than about 70 kDa will experience lengthened plasma half-life. For proteins larger than 70 kDa, the effects of the polyethylene glycol and its molecular weight will vary with its clearance mechanism.

In general, using a polyethylene glycol having a high molecular weight in the processes of the present invention results in conjugated proteins having more polyethylene glycol per molecule of protein than using polyethylene glycol having a lower molecular weight. Thus, when a high amount of polyethylene glycol per protein molecule is desirable, the molecular weight of the polyethylene glycol is preferably up to 20,000. However, smaller molecular weight polyethylene glycols, because of their greater solution mobility, may conjugate to more sites on the protein than a higher molecular protein. Thus, when a protein has a number of desired conjugation sites it may be preferable to use a polyethylene glycol having a lower molecular weight to assure that an optimum number of sites is conjugated. This may be a particularly desirable approach when the potential conjugation sites or reaction site on the protein are in close proximity to each other. Another consideration used in selecting a polyethylene glycol molecular weight is that even though proteins treated in accordance with the present invention have protected sites, larger molecular weight polyethylene glycols may be so large that, once conjugated, their molecular size causes them to extend their spacial or steric influence so that binding or receptor sites have reduced accessibility. It is within the knowledge of those skilled in the art to determine an optimum polyethylene glycol molecular weight for any selected protein and benefits desired from the polyethylene glycol conjugation.

While the above described polyethylene glycol conjugation procedures are those in which the result is polyethylene glycol conjugated to protein via a covalent bond, it is within the scope of the present invention to include procedures in which the conjugation is via a different association. In the context of the present invention, proteins may be modified by conjugating them to polyethylene glycol using a variety of different linking or conjugating mechanisms. For example, a protein selected for conjugation can be derivatized at an amino group or other suitably reactive functionality with a polyA oligonucleotide and then conjugated with a polyethylene glycol derivatized with a polyT oligonucleotide. Another approach involves derivatizing the protein with a functionality having a known specific binding partner and then conjugating the protein with polyethylene glycol which has been derivatized with the binding partner for the functionality. For example, a protein can be derivatized with biotin and the polyethylene glycol derivatized with streptavidin or avidin (or vice versa). This results in the specific binding of polyethylene glycol to those protein sites having the biotin. A number of reagents for modifying proteins for the purpose of introducing certain functionalities are commercially available. For example, the Pierce ImmunoTechnology catalogue identifies and provides access to a variety of reagents associated with protein modification. Among these are Traut's Reagents and SATA (Pierce ImmunoTechnology Catalogue, Vol I, pg E-14) which can introduce active groups at N-terminal amines and lysine amino functionalities. These active groups provide sites for further introducing functionalities for reacting more specifically with polyethylene glycol. Those skilled in the art will also recognize that ionic interactions between polyethylene glycol and a protein of interest are also possible. For example, an association between an ionic moiety on the protein and its counter ion on polyethylene glycol can be utilized if the association is sufficiently strong to remain associated under physiological conditions.

Further embodiments of the present invention which may utilize prior modified proteins include those processes in which the protein selected for conjugation has too few potential polyethylene glycol conjugation sites or no potential polyethylene glycol conjugation sites outside the protected amino acid region. By modifying the selected protein to introduce amino and sulfhydryl sites on the protein sufficient polyethylene glycol may be conjugated to the selected protein to provide the desired benefits. Modifying the selected protein can be achieved using genetic engineering methodologies or chemical modification. As mentioned above, processes and reagents for modifying proteins to achieve a large variety of desired results are well known in the art. In particular, in Wong, *Chemistry of Protein Conjugation and Cross-linking*, CRC Press, 1993, incorporated herein by reference, provides information relating to conjugation reagents and process conditions.

While polyethylene glycol is a preferred protein conjugating reactant, a variety of additional polymer modifiers have been used to modify proteins. These include modified polyethylene glycols, branched polyethylene glycols, crosslinked polyethylene glycols, dextrans, polyvinylpyrrolidone, polyvinylalcohol, polyamino acids, albumin and gelatins. Those skilled in the art will appreciate, once having an understanding of the present invention, that the principles and methods described herein can be applied to processes for modifying proteins with any of these additional reagents.

Proteins modified according to the procedures described herein have benefits associated with polyethylene glycol conjugation without the expected significant loss in activity. By merely applying known testing procedures to establish post conjugation activity, the benefits to proteins conjugated in accordance with the present invention can be demonstrated. Activity tests are specific for the protein and should be selected according to the protein of interest. Many proteins have more than one site associated with one or more activities The choice of activity for measurement for such proteins depends upon the activity of interest and the site which is specifically selected for the amino acid residue deletion and subsequent conjugation reaction. In addition to evaluating polyethylene glycol conjugated proteins for their activity, they can be analyzed for the degree of polyethylene glycol substitution, molecular weight, and sites of conjugation. Techniques for performing these analytical procedures are well known and some are described with respect to polyethylene glycol conjugated proteins in *Critical Reviews in Therapeutic Drug Carrier Systems*, 9(3:4):285–291, 1992. Example 4–6 describe exemplary methods for characterizing polyethylene glycol conjugated proteins.

In addition to providing compounds having improved bioactivity characteristics, the processes of the present invention provide polyethylene glycol conjugated molecule product that is more homogeneous and in higher yields. Because conjugation will not take place at amino acid residues that are critical to the molecule's bioactivity, the reaction product need not be purified by cutting out numerous unwanted product fractions. Because the polyethylene glycol reaction can be taken to completion and all the available polyethylene glycol sites can be fully reacted, the final product is more homogeneous than prior art products which are prepared under conditions that favor reaction at specific sites.

The following examples are presented in order to provide a more detailed description of specific embodiments of the present invention and are not to be construed as limiting the scope of the invention.

EXAMPLE 1

Selecting a Protein Modification Site

The following describes a procedure for identifying amino acid residues of p75 TNF receptor for deletion and substitution in accordance with the present invention. Because the expected polyethylene glycol modification reaction conditions were to be those that favor modification of the ε-amino group of lysine residues and the N-terminal amine, the amino acids identified were lysine residues that make contact between the TNF receptor and the ligand in the TNF receptor-ligand complex.

The p75 TNF receptor is from a family of structurally homologous receptors which includes the p55 TNF receptor. TNFα and TNFβ (TNF ligands) compete for binding to the p55 and p75 TNF receptors. The x-ray crystal structure of the complex formed by the extracellular domain of the human p55 TNF receptor and TNFβ has been determined (Banner et al. *Cell* 73:431, 1993, incorporated herein by reference). This crystallography work confirmed that the complex of p55 TNF receptor and TNFβ has three p55 TNF receptor molecules bound symmetrically to one TNFβ trimer. The studies further demonstrated that the receptor binds in a groove between two adjacent TNFβ subunits. Advantageously, the crystal structure of the complex provides a model for TNF receptor structure and activation and can be used to identify amino acid domains within the ligand and in the receptor that make contact to for the complex.

A sequence alignment of the p55 TNF receptor amino acid sequence and the p75 TNF receptor amino acid sequence reveals that p75 TNF receptor residues K34, K42, K47, K108, K120, and K140 are closely aligned with p55 TNF receptor residues K32, Y40, G45, S108, L119 and T138. (See Banner et al. *Cell* 73:431, 1993). Based upon this alignment information and molecular modeling that illustrates the spatial positions of lysine residues on p75 TNF receptor, it can be seen that two lysine residues on the p75 receptor make contact between the p75 receptor and ligand. These lysine residues are K108 and K120 (the lysine at position 108 and the lysine at position 120). FIG. 1 provides an amino acid sequence of the extracellular domain of p75 TNF receptor (without the signal sequence) and illustrates lysine residues that are polyethylene glycol conjugation sites and lysine residues that make contact with TNFα. Thus, the lysine residues at positions 108 and 120 were selected for deletion and substitution in accordance with this invention.

EXAMPLE 2

Preparing Wildtype p75TNF Receptor and Mutant p75 TNF Receptor

The following describes processes for preparing a wildtype soluble p75 TNF Receptor molecule (extracellular domain of p75 TNF receptor) and three mutant soluble TNF receptor molecules. The wildtype soluble p75 TNF Receptor has the nucleotide and amino acid sequences described in SEQ ID NO:7 and SEQ ID NO:8. The wildtype and mutant TNF receptor molecules utilized in the following experiments were the extracellular domains without the signal peptide.

The soluble p75 TNF receptor in the form of a covalently dimerized fusion construct of two extracellular, ligand binding portions of the human p75 TNF receptor fused together by an IgG1Fc moiety (TNFR:Fc) (Mohler et al. *J. Immunol.* 151:1548–1561, 1993) was prepared by expressing the protein in CHO cells using the dihydrofolate reductase selectable amplifiable marker. Suspension cells were centrifuged and resuspended into serum-free medium in a controlled bioreactor. The product was collected after 7 days and the TNFR:Fc molecule was purified using protein A affinity chromatography followed by an ion-exchange chromatography step.

For each of the three mutant soluble TNF receptor molecules a specific lysine, K, was deleted and an arginine, R, was engineered in the same position. More specifically, the lysine at position 108 and/or the lysine at position 120 were mutated individually so that two single mutants (K108R or K120R) and one double mutant (K108R, K120R) were prepared in which the K at position 108 and/or position 120 was replaced by an R at the same position. SEQ ID NO:1 provides the nucleotide sequence for the K108R mutant and SEQ ID NO:2 describes the amino acid sequence encoded by SEQ ID NO:1. SEQ ID NO:3 provides the nucleotide sequence for the K120 R mutant and SEQ ID NO:4 describes the amino acid sequences encoded by SEQ ID NO:3. SEQ ID NO:5 provides the nucleotide sequence for the K108R, K120R mutant and SEQ ID NO:6 describes the amino acid sequences encoded by SEQ ID NO:5.

Briefly, the mutants were prepared using site directed mutagenesis of K108 and/or K120 in the human p75 TNF receptor using PCR mutagenesis of the Sfr1-Not1 fragment of hTNF receptor and Fc fusion protein (hTNFR:Fc). The mutant TNF receptor fragments were ligated in frame with a human Fc fragment in the mammalian expression vector sf Haveo409. Several of the prepared clones were sequence to confirm that the desired nucleic acid changes were incorporated into the mutein nucleotide sequences.

More particularly, PCR mutagenesis was used to generate mutated 430 base pair Sal/Sfr1 fragments. The PCR mutagenesis procedures utilized wild type TNFR cDNA (SEQ ID NO:7) used as the template for the PCR reactions. The oligonucleotide sequences used in the PCR reactions to generate the 3 mutant Sal1-Srf1 DNA fragments were as follows:

For the TNF receptor (K108R) mutant the 3' oligonucleotide contained an A to G substitution at position 389 and a Srf1 site at the 3' end. For the TNF receptor (K120R) mutant the 3' oligonucleotide contained an A to G substitution at position 425 and a Srf1 site at the 3' end. For the TNF receptor (K108R,K120R) mutant the oligonucleotide contained an A to G substitution at position 389 and 425 and a Srf1 site at the 3' end. The 5' oligonucleotide used to generate the mutant PCR DNA fragments had no nucleotide changes in the TNFR coding nucleotides and contained the 5' Sal1 site.

For the PCR Reactions the Boehringer Mannheim Expand High Fidelity PCR kit and reagents were used according to manufacturer's directions. The PCR cycling protocol involved the following conditions: 94° C. for 2 minutes; 94° C. for 30 seconds; 50° C. for 15 seconds, 72° C. for 1 minute. 25 cycle reaction.

The DNA fragments generated in the PCR reactions were separated on a 1% agarose gel and the 430 base pair TNFR fragments were isolated using GeneClean reagent from BIO 101. The isolated fragments were restriction digested with Sal1 and Srf1 from NEB in Universal Restriction Buffer from Stratagene. The DNA was then repurified using the GeneClean reagents from BIO101.

Each of the mutant Sal1/Srf1 DNA 430 fragments generated above (and corresponding to the 5' end of the TNF receptor) was individually ligated with the 1065 basepair Srf1/Not1 DNA fragment corresponding to the 3' TNF receptor and human Fc cDNA and the 7730 basepair Sal1/Not1 pDC409 expression. 20ng of the pDC409 vector was used for each ligated reaction and the TNF receptor fragments were present at a 3-fold higher molar concentration. The ligation reaction was done in Boehringer Mannheim ligation mix with 500 units of ligase enzyme at room temperature for 3 hours.

The ligation reaction mixtures were dialyzed and 1/10 of the reaction mixture was electroporated into *E. coli* DH10B cells. 10 colonies from each construction were grown in liquid culture and the expression vector constructs was confirmed using restriction enzyme analysis. The TNF receptor cDNA insert in one construct of each of the 3 mutants was analyzed by nucleotide sequencing to confirm the desired nucleotide mutations.

The three mutant fusion cDNA constructs were transfected into CVI/EBNA cells. The transfected cells were cultured at 37° C. for 7 days and then conditioned media from these cells was harvested and monitored for TNFR:Fc expression using an Fc ELISA assay. The conditioned media was also monitored for TNF receptor bioactivity using an A375 cell growth bioassay that is based upon measuring inhibition of TNF activity. The three TNFR:Fc mutants and the TNFR:Fc wildtype construct demonstrated similar receptor molecule expression levels.

In order to collect and purify the mutant TNF receptor proteins, supernatants from the transfected CV1/EBNA cells were collected 7 days post transfection and clarified by centrifugation and filtration through a 0.45 $\mu$m filter. Purification of the collected and filtered wild type protein and the mutant proteins was carried out using protein A affinity chromatography. A protein A sepharose column was used to capture the Fc portion of the fusion proteins. Once bound, the protein was washed with 3 column volumes of 25 mM TRIS/140 mM NaCl at pH7.4 and eluted with 3 columns volumes of 50 mM sodium acetate/100 mM NaCl at pH 4.0. Each eluted fusion protein was dialyzed against 20 mM $Na_2HPO_4$ at pH 7.4 and diluted to approximately 1 mg/mL. The final collected products were purified soluble p75 TNFR:Fc mutants as described above. SEQ ID NO:1 provides the nucleotide sequence for the K108R mutant and SEQ ID NO:2 describes the amino acid sequence encoded by SEQ ID NO:1. SEQ ID NO:3 provides the nucleotide sequence for the K120R mutant and SEQ ID NO:4 describes the amino acid sequences encoded by SEQ ID NO:3. SEQ ID NO:5 provides the nucleotide sequence for the K108R, K120 R mutant and SEQ ID NO:6 describes the amino acid sequences encoded by SEQ ID NO:5.

EXAMPLE 3

Conjugating Wildtype and Mutant p75 TNF:Fc Receptors with Polyethylene Glycol

The following describes a process for preparing polyethylene glycol conjugated wildtype TNFR:Fc molecules and polyethylene glycol conjugated mutant TNFR:Fc molecules. For each polyethylene glycol conjugation reaction, a one hundred micrograms (100 $\mu$g) portion of wildtype TNFR:Fc, or mutant TNFR:Fc, prepared in Example 2 was dissolved in 400 $\mu$L of 50 mM $Na_2HPO_4$ at pH 8.5 and allowed to react with SPA-PEG 5000 at different molar ratios of polyethylene glycol to protein (calculated as number of lysine residues in TNFR:Fc) overnight at 4° C. The molar ratios of protein to lysine residues 1:1 and 10:1. SPA-PEG is a 5,000 MW succinimidyl carbonate activated monomethoxypolyethylene glycol purchased from Shearwater Polymers, Birmingham, Ala. The protein and polyethylene glycol solutions were allowed to react overnight at 2–8° C.

Each of the polyethylene glycol conjugated TNFR:Fc molecules was purified by ion exchange chromatography using SP Sepharose Fast Flow resin (Pharmacia) equilibrated with 20 mM sodium phosphate, pH 7.4. Polyethylene glycol conjugated TNFR:Fc bound to the resin under these conditions. Unreacted polyethylene glycol and reaction byproducts were rinsed from the column with 5 column volumes of the equilibration buffer. The polyethylene glycol conjugated TNFR:Fc was eluted from the column with five column volumes of 20 mM sodium phosphate, 200 mM NaCl, pH 7.4. The eluted fractions were pooled and concentrated to approximately 1–5 mg/mL.

The following indicates the designation given each of the TNFR:Fc molecules conjugated with polyethylene glycol (PEG) by the above described procedure:

1. PEG-TNFR:Fc(K108R, K120R);
2. PEG-TNFR:Fc(K108R);
3. PEG-TNFR:Fc(K120R);
4. PEG-TNFR:Fc.

EXAMPLE 4

Characterization of Conjugated TNFR:Fc

The following describes the characterization of polyethylene glycol conjugated wildtype polyethylene glycol conjugated mutant TNFR:Fc molecules prepared in Example 3 and a control characterization of unconjugated wildtype and mutant TNFR:Fc molecules prepared in Example 2. The characterization analyses included SDS-polyacrylamide gel electrophoresis, size exclusion chromatography, ELISA and in vitro bioassay testing.

SDS-PAGE gradient gels of 4–20% acrylamide (Novex, San Diego) were run with 1 µg of each polyethylene glycol conjugated mutant TNFR:Fc molecule and polyethylene glycol conjugated wildtype TNFR:Fc. The gels were stained with Novex fast stain according to manufacturer's instructions. The gradient gels showed that the degree of polyethylene glycol conjugation was similar for each of the polyethylene glycol conjugated mutant TNFR:Fc molecules and the polyethylene glycol conjugated wildtype TNFR:Fc molecule.

Size exclusion chromatography was performed on each of the molecules conjugated with polyethylene glycol as described in Example 3. The size exclusion characterization was performed using a Waters HPLC system from Millipore Corp. Milford, Mass. that was equipped with a 300×8 mm SEC-400 Biosil column from BioRad. Sample injection sizes were 50–100 µg and the mobile phase was phosphate; buffered saline at 1 mL/min. The results confirmed that the polyethylene glycol conjugated mutants and the polyethylene glycol conjugated wildtype TNFR:Fc had substantial increases in overall size. More particularly, depending upon the ratio of polyethylene glycol to lysine used in the conjugation reaction, the polyethylene glycol conjugated molecules were 2–3 times larger than the unconjugated molecules.

The polyethylene glycol conjugated mutant TNFR:Fc molecules, the polyethylene glycol conjugated wildtype TNFR:Fc molecule and unconjugated forms of TNFR:Fc were subjected to ELISA testing that involved coating 96 well microtiter plates with anti-IgG1-Fc monoclonal antibodies, applying the polyethylene glycol modified molecules to the microtiter plates and allowing them to bind with the anti-IgG1-Fc antibodies. A secondary polyclonal anti-TNFR antibody was used to detect the quantity of polyethylene glycol conjugated molecules and the quantity of unconjugated TNFR:Fc bound to the plate. The results of these studies demonstrated that the polyethylene glycol conjugated mutant TNFR:Fc and polyethylene conjugated wildtype TNFR:Fc reduced or eliminated binding with anti-IgG1-Fc and/or anti-TNFR antibodies. The results suggest that polyethylene glycol conjugation shields epitopes that are active in antibody binding.

EXAMPLE 5

Pharmacokinetics of Wildtype and Mutant TNFR:Fc Molecules

The following describes experiments designed to compare the pharmacokinetics of wildtype TNFR:Fc with the polyethylene glycol conjugated TNFR:Fc mutant molecule K108R,K120R (the lysine at 108 and 120 substituted with arginine). The mutant molecule had been conjugated with a polyethylene glycol:lysine ration of 10:1.

Groups of 2 10–12 week old female BALB/c mice were injected intravenously with 10 µg of wildtype TNFR:Fc or conjugated mutant TNFR:Fc in a total volume of 100 µL. Following the injection, mice were sacrificed and blood samples were collected at 5 minutes, 1 hour, 8 hours, 24 hours, 48 hours and 72 hours via cardiac puncture. Plasma samples were analyzed by A375 bioassay. The elimination half lives, t½, of the polyethylene conjugated mutant and the wildtype TNFR:Fc were determined. The half-life values are presented as t½+/−S.E. were S.E. indicates the standard error in fitting the log linear line to the data points. The t½ of wildtype TNFR:Fc was determined to be 16.5+/−1.0 hours and that of the polyethylene glycol mutant was determined to be 36.5+/−8.5 hours.

The results of the above experiments demonstrate that polyethylene glycol conjugated TNF receptor prepared in accordance with the present invention has a significantly enhanced circulation half life compared to a TNF receptor that is not polyethylene glycol conjugated.

EXAMPLE 6

Bioactivity of Polyethylene Conjugated Wild Type TNFR:Fc and Polyethylene Conjugated Mutant TNFR:Fc The bioactivities of the polyethylene glycol conjugated TNFR:Fc molecules prepared in Example 3 were measured by in vitro A375 bioassays. This assay is generally described in Onozaki et al. *J. Immunology* 135:3962 (1985) and Nakai et al. *Biochem. Biophys. Res. Comm.* 154:1189 (1988). The bioassay is based upon the inhibitory response of the A375 human malignant melanoma adherent cell line to TNFα. Soluble TNFR:Fc can specifically neutralize the inhibitory activity of TNFα in a dose dependent manner. To perform the bioassay, 375 cell line (ATCC CRL 1872) was harvested using a trypsin-EDTA solution to remove the cell monolayer from flasks. The harvested cells were washed with an assay medium of Dulbeccos' Modified Eagles Medium with added fetal bovine serum, non-essential amino acids, and sodium pyruvate (all purchased from GIBCO).

Ninety-six well plates were prepared with serial dilutions of working solutions of the polyethylene glycol conjugated mutant TNFR:Fc described in Example 3. Then, equal amounts of TNFα (R & D Systems, Cat. No. #210-CA TF) in the assay medium described above were added to wells in 96 well plates followed by adding an equal volume of about $4\times10^5$ harvested cell suspension to each well.

The plates were placed in a humidity chamber at 37° C. and 10% $CO_2$ and the cells were allowed to incubate for 72 hours. Then the plates were removed from the chamber and the cells were washed with PBS solution, blotted, and fixed with ethyl alcohol. Viable cells were made visible by staining the fixed cells with 0.1% aqueous crystal violet solution. After washing the plates with water and blotting the cells, 2% sodium deoxycholate solution was added to each well and the wells of each plate were read for optical density at 570 nm on a plate reader using Delta Soft microplate analysis software. Standard bioactivity units were assigned for each sample and adjusted to take into account the concentration of TNFR:Fc in the wells. Wells containing blanks were assigned a bioactivity of zero.

The results of the A375 bioassays demonstrated the following order of activity for the polyethylene glycol conjugated molecules:

PEG-TNFR:Fc(K108R,K120R,)>PEG-TNFR:Fc(K108R)>>PEG-TNFR:Fc(K120R)=PEG-TNFR:Fc (PEG=>polyethylene glycol conjugated)

The results indicate that the polyethylene glycol conjugated TNFR:Fc molecules retain significant biological activity as determined by in vitro methods. Because the TNFR:Fc mutein PEG-TNFR:Fc(108R), in which the lysine at position 108 was mutated to arginine, retains much greater activity than the mutein in which the lysine at 120 is mutated to arginine, it is suggested the polyethylene glycol conjugated to K108 interferes with TNF binding. When this residue is mutated to R108, polyethylene conjugation at the 108 position is prevented and does not significantly reduce TNF binding activity.

What is claimed is:

1. A polyethylene conjugated nutant polypeptide, wiherein the mutant polypeptide is selected from the group consisting of SEQ ID NO:2, SEQ ID NO:4 and SEQ ID NO:6.

2. A process for modifying p75 TNFR, said process comprising the steps of:

replacing the lysine at amino acid 108 and amino acid 120 of SEQ ID NO:8 with an arginine; and contacting the p75 TNFR having replaced lysine residues with polyethylene glycol under conditions sufficient to conjugate the polyethylene glycol to the p75 TNFR by reacting the polyethylene glycol with lysine residues.

3. A polyethylene glycol conjugated p75 TNFR prepared according to the process of claim 2.

4. A polyethlylene conjngated polypeptide, wherein the polypeptide comprise the amino acid sequence of SEQ ID NO:2.

5. A polyethylene conjugated polypeptide, wherein the polypeptide comprises the amino acid sequence of SEQ ID NO:4.

6. A polyethylene conjugated polypeptide, wherein the polypeptide comprises the amino acid sequence of SEQ ID NO:6.

7. A process for modifying p75TNFR, said process comprising the steps of:

replacing the lysine at amino acid 108 with an arginine; and, contacting the p75 INFR having replaced lysine residues with polyethylene glycol under conditions sufficient to conjugate the polyethylene glycol to p75 TNFR by reacting the polyethylene glycol with lysine residues.

8. A process for modifying p75TNFR, said process comprising the steps of:

replacing the lysine at amino acid 120 with an arginine; and, contacting the p75 TFR having replaced lysine residues with polyethylene glycol under conditions sufficient to conjugate the polyethylene glycol to p75 TNFR by reacting the polyethylene glycol with lysine residues.

9. A polyethylene glycol conjugated p75 TNFR prepared according to the process of claim 7.

10. A polyethylene glycol conjugated p75 TNFR prepared according to the process of claim 8.

* * * * *

```
                             SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 705 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
          (A) NAME/KEY: CDS
          (B) LOCATION: 1..705

(xi) SEQUENCE DESCRIPTION: SEQ ID NO:1:

TTG CCC GCC CAG GTG GCA TTT ACA CCC TAC GCC CCG GAG CCC GGG AGC        48
Leu Pro Ala Gln Val Ala Phe Thr Pro Tyr Ala Pro Glu Pro Gly Ser
  1               5                  10                  15

ACA TGC CGG CTC AGA GAA TAC TAT GAC CAG ACA GCT CAG ATG TGC TGC        96
Thr Cys Arg Leu Arg Glu Tyr Tyr Asp Gln Thr Ala Gln Met Cys Cys
             20                  25                  30

AGC AAA TGC TCG CCG GGC CAA CAT GCA AAA GTC TTC TGT ACC AAG ACC       144
Ser Lys Cys Ser Pro Gly Gln His Ala Lys Val Phe Cys Thr Lys Thr
         35                  40                  45

TCG GAC ACC GTG TGT GAC TCC TGT GAG GAC AGC ACA TAC ACC CAG CTC       192
Ser Asp Thr Val Cys Asp Ser Cys Glu Asp Ser Thr Tyr Thr Gln Leu
     50                  55                  60

TGG AAC TGG GTT CCC GAG TGC TTG AGC TGT GGC TCC CGC TGT AGC TCT       240
Trp Asn Trp Val Pro Glu Cys Leu Ser Cys Gly Ser Arg Cys Ser Ser
 65                  70                  75                  80

GAC CAG GTG GAA ACT CAA GCC TGC ACT CGG GAA CAG AAC CGC ATC TGC       288
Asp Gln Val Glu Thr Gln Ala Cys Thr Arg Glu Gln Asn Arg Ile Cys
                 85                  90                  95

ACC TGC AGG CCC GGC TGG TAC TGC GCG CTG AGC AGG CAG GAG GGG TGC       336
Thr Cys Arg Pro Gly Trp Tyr Cys Ala Leu Ser Arg Gln Glu Gly Cys
            100                 105                 110

CGG CTG TGC GCG CCG CTG CGC AAG TGC CGC CCG GGC TTC GGC GTG GCC       384
Arg Leu Cys Ala Pro Leu Arg Lys Cys Arg Pro Gly Phe Gly Val Ala
```

```
                    115                     120                         125
AGA CCA GGA ACT GAA ACA TCA GAC GTG GTG TGC AAG CCC TGT GCC CCG           432
Arg Pro Gly Thr Glu Thr Ser Asp Val Val Cys Lys Pro Cys Ala Pro
    130                     135                     140

GGG ACG TTC TCC AAC ACG ACT TCA TCC ACG GAT ATT TGC AGG CCC CAC           480
Gly Thr Phe Ser Asn Thr Thr Ser Ser Thr Asp Ile Cys Arg Pro His
145                     150                     155                 160

CAG ATC TGT AAC GTG GTG GCC ATC CCT GGG AAT GCA AGC ATG GAT GCA           528
Gln Ile Cys Asn Val Val Ala Ile Pro Gly Asn Ala Ser Met Asp Ala
                    165                     170                 175

GTC TGC ACG TCC ACG TCC CCC ACC CGG AGT ATG GCC CCA GGG GCA GTA           576
Val Cys Thr Ser Thr Ser Pro Thr Arg Ser Met Ala Pro Gly Ala Val
                180                     185                 190

CAC TTA CCC CAG CCA GTG TCC ACA CGA TCC CAA CAC ACG CAG CCA ACT           624
His Leu Pro Gln Pro Val Ser Thr Arg Ser Gln His Thr Gln Pro Thr
        195                     200                 205

CCA GAA CCC AGC ACT GCT CCA AGC ACC TCC TTC CTG CTC CCA ATG GGC           672
Pro Glu Pro Ser Thr Ala Pro Ser Thr Ser Phe Leu Leu Pro Met Gly
    210                     215                 220

CCC AGC CCC CCA GCT GAA GGG AGC ACT GGC GAC                               705
Pro Ser Pro Pro Ala Glu Gly Ser Thr Gly Asp
225                     230                 235

(2) INFORMATION FOR SEQ ID NO:2:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:2:

Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Arg Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
```

```
                195                 200                    205
Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```

(2) INFORMATION FOR SEQ ID NO:3:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..705

(xi) SEQUENCE DESCRIPTION: SEQ ID NO:3:

```
TTG CCC GCC CAG GTG GCA TTT ACA CCC TAC GCC CCG GAG CCC GGG AGC        48
Leu Pro Ala Gln Val Ala Phe Thr Pro Tyr Ala Pro Glu Pro Gly Ser
 1               5                  10                  15

ACA TGC CGG CTC AGA GAA TAC TAT GAC CAG ACA GCT CAG ATG TGC TGC        96
Thr Cys Arg Leu Arg Glu Tyr Tyr Asp Gln Thr Ala Gln Met Cys Cys
            20                  25                  30

AGC AAA TGC TCG CCG GGC CAA CAT GCA AAA GTC TTC TGT ACC AAG ACC       144
Ser Lys Cys Ser Pro Gly Gln His Ala Lys Val Phe Cys Thr Lys Thr
        35                  40                  45

TCG GAC ACC GTG TGT GAC TCC TGT GAG GAC AGC ACA TAC ACC CAG CTC       192
Ser Asp Thr Val Cys Asp Ser Cys Glu Asp Ser Thr Tyr Thr Gln Leu
    50                  55                  60

TGG AAC TGG GTT CCC GAG TGC TTG AGC TGT GGC TCC CGC TGT AGC TCT       240
Trp Asn Trp Val Pro Glu Cys Leu Ser Cys Gly Ser Arg Cys Ser Ser
65                  70                  75                  80

GAC CAG GTG GAA ACT CAA GCC TGC ACT CGG GAA CAG AAC CGC ATC TGC       288
Asp Gln Val Glu Thr Gln Ala Cys Thr Arg Glu Gln Asn Arg Ile Cys
                85                  90                  95

ACC TGC AGG CCC GGC TGG TAC TGC GCG CTG AGC AAG CAG GAG GGG TGC       336
Thr Cys Arg Pro Gly Trp Tyr Cys Ala Leu Ser Lys Gln Glu Gly Cys
            100                 105                 110

CGG CTG TGC GCG CCG CTG CGC AGG TGC CGC CCG GGC TTC GGC GTG GCC       384
Arg Leu Cys Ala Pro Leu Arg Arg Cys Arg Pro Gly Phe Gly Val Ala
        115                 120                 125

AGA CCA GGA ACT GAA ACA TCA GAC GTG GTG TGC AAG CCC TGT GCC CCG       432
Arg Pro Gly Thr Glu Thr Ser Asp Val Val Cys Lys Pro Cys Ala Pro
    130                 135                 140

GGG ACG TTC TCC AAC ACG ACT TCA TCC ACG GAT ATT TGC AGG CCC CAC       480
Gly Thr Phe Ser Asn Thr Thr Ser Ser Thr Asp Ile Cys Arg Pro His
145                 150                 155                 160

CAG ATC TGT AAC GTG GTG GCC ATC CCT GGG AAT GCA AGC ATG GAT GCA       528
Gln Ile Cys Asn Val Val Ala Ile Pro Gly Asn Ala Ser Met Asp Ala
                165                 170                 175

GTC TGC ACG TCC ACG TCC CCC ACC CGG AGT ATG GCC CCA GGG GCA GTA       576
Val Cys Thr Ser Thr Ser Pro Thr Arg Ser Met Ala Pro Gly Ala Val
            180                 185                 190
```

```
CAC TTA CCC CAG CCA GTG TCC ACA CGA TCC CAA CAC ACG CAG CCA ACT      624
His Leu Pro Gln Pro Val Ser Thr Arg Ser Gln His Thr Gln Pro Thr
        195                 200                 205

CCA GAA CCC AGC ACT GCT CCA AGC ACC TCC TTC CTG CTC CCA ATG GGC      672
Pro Glu Pro Ser Thr Ala Pro Ser Thr Ser Phe Leu Leu Pro Met Gly
    210                 215                 220

CCC AGC CCC CCA GCT GAA GGG AGC ACT GGC GAC                          705
Pro Ser Pro Pro Ala Glu Gly Ser Thr Gly Asp
225                 230                 235
```

(2) INFORMATION FOR SEQ ID NO:4:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:4:

```
Leu Pro Ala Gln Val Ala Phe Thr Pro Tyr Ala Pro Glu Pro Gly Ser
  1                 5                  10                  15

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
     50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
                100                 105                 110

Arg Leu Cys Ala Pro Leu Arg Arg Cys Arg Pro Gly Phe Gly Val Ala
            115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```

(2) INFORMATION FOR SEQ ID NO:5:

(i) SEQUENCE CHARACTERISTICS:
        (A) LENGTH: 705 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
    (A) NAME/KEY: CDS
    (B) LOCATION: 1..705

(xi) SEQUENCE DESCRIPTION: SEQ ID NO:5:

```
TTG CCC GCC CAG GTG GCA TTT ACA CCC TAC GCC CCG GAG CCC GGG AGC      48
Leu Pro Ala Gln Val Ala Phe Thr Pro Tyr Ala Pro Glu Pro Gly Ser
 1               5                  10                  15

ACA TGC CGG CTC AGA GAA TAC TAT GAC CAG ACA GCT CAG ATG TGC TGC      96
Thr Cys Arg Leu Arg Glu Tyr Tyr Asp Gln Thr Ala Gln Met Cys Cys
             20                  25                  30

AGC AAA TGC TCG CCG GGC CAA CAT GCA AAA GTC TTC TGT ACC AAG ACC     144
Ser Lys Cys Ser Pro Gly Gln His Ala Lys Val Phe Cys Thr Lys Thr
         35                  40                  45

TCG GAC ACC GTG TGT GAC TCC TGT GAG GAC AGC ACA TAC ACC CAG CTC     192
Ser Asp Thr Val Cys Asp Ser Cys Glu Asp Ser Thr Tyr Thr Gln Leu
     50                  55                  60

TGG AAC TGG GTT CCC GAG TGC TTG AGC TGT GGC TCC CGC TGT AGC TCT     240
Trp Asn Trp Val Pro Glu Cys Leu Ser Cys Gly Ser Arg Cys Ser Ser
 65                  70                  75                  80

GAC CAG GTG GAA ACT CAA GCC TGC ACT CGG GAA CAG AAC CGC ATC TGC     288
Asp Gln Val Glu Thr Gln Ala Cys Thr Arg Glu Gln Asn Arg Ile Cys
                 85                  90                  95

ACC TGC AGG CCC GGC TGG TAC TGC GCG CTG AGC AGG CAG GAG GGG TGC     336
Thr Cys Arg Pro Gly Trp Tyr Cys Ala Leu Ser Arg Gln Glu Gly Cys
            100                 105                 110

CGG CTG TGC GCG CCG CTG CGC AGG TGC CGC CCG GGC TTC GGC GTG GCC     384
Arg Leu Cys Ala Pro Leu Arg Arg Cys Arg Pro Gly Phe Gly Val Ala
        115                 120                 125

AGA CCA GGA ACT GAA ACA TCA GAC GTG GTG TGC AAG CCC TGT GCC CCG     432
Arg Pro Gly Thr Glu Thr Ser Asp Val Val Cys Lys Pro Cys Ala Pro
    130                 135                 140

GGG ACG TTC TCC AAC ACG ACT TCA TCC ACG GAT ATT TGC AGG CCC CAC     480
Gly Thr Phe Ser Asn Thr Thr Ser Ser Thr Asp Ile Cys Arg Pro His
145                 150                 155                 160

CAG ATC TGT AAC GTG GTG GCC ATC CCT GGG AAT GCA AGC ATG GAT GCA     528
Gln Ile Cys Asn Val Val Ala Ile Pro Gly Asn Ala Ser Met Asp Ala
                165                 170                 175

GTC TGC ACG TCC ACG TCC CCC ACC CGG AGT ATG GCC CCA GGG GCA GTA     576
Val Cys Thr Ser Thr Ser Pro Thr Arg Ser Met Ala Pro Gly Ala Val
            180                 185                 190

CAC TTA CCC CAG CCA GTG TCC ACA CGA TCC CAA CAC ACG CAG CCA ACT     624
His Leu Pro Gln Pro Val Ser Thr Arg Ser Gln His Thr Gln Pro Thr
        195                 200                 205

CCA GAA CCC AGC ACT GCT CCA AGC ACC TCC TTC CTG CTC CCA ATG GGC     672
Pro Glu Pro Ser Thr Ala Pro Ser Thr Ser Phe Leu Leu Pro Met Gly
    210                 215                 220

CCC AGC CCC CCA GCT GAA GGG AGC ACT GGC GAC                         705
Pro Ser Pro Pro Ala Glu Gly Ser Thr Gly Asp
225                 230                 235
```

(2) INFORMATION FOR SEQ ID NO:6:

(i) SEQUENCE CHARACTERISTICS:
        (A) LENGTH: 235 amino acids
        (B) TYPE: amino acid (D) TOPOLOGY: linear (ii) MOLECULE TYPE: protein (xi) SEQUENCE DESCRIPTION: SEQ ID NO:6:

Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
        50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Arg Gln Glu Gly Cys
            100                 105                 110

Arg Leu Cys Ala Pro Leu Arg Arg Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

(2) INFORMATION FOR SEQ ID NO:7:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 1..705

(xi) SEQUENCE DESCRIPTION: SEQ ID NO:7:

TTG CCC GCC CAG GTG GCA TTT ACA CCC TAC GCC CCG GAG CCC GGG AGC         48
Leu Pro Ala Gln Val Ala Phe Thr Pro Tyr Ala Pro Glu Pro Gly Ser
 1               5                  10                  15

ACA TGC CGG CTC AGA GAA TAC TAT GAC CAG ACA GCT CAG ATG TGC TGC         96

```
Thr Cys Arg Leu Arg Glu Tyr Tyr Asp Gln Thr Ala Gln Met Cys Cys
         20                  25                  30

AGC AAA TGC TCG CCG GGC CAA CAT GCA AAA GTC TTC TGT ACC AAG ACC      144
Ser Lys Cys Ser Pro Gly Gln His Ala Lys Val Phe Cys Thr Lys Thr
         35                  40                  45

TCG GAC ACC GTG TGT GAC TCC TGT GAG GAC AGC ACA TAC ACC CAG CTC      192
Ser Asp Thr Val Cys Asp Ser Cys Glu Asp Ser Thr Tyr Thr Gln Leu
     50                  55                  60

TGG AAC TGG GTT CCC GAG TGC TTG AGC TGT GGC TCC CGC TGT AGC TCT      240
Trp Asn Trp Val Pro Glu Cys Leu Ser Cys Gly Ser Arg Cys Ser Ser
 65                  70                  75                  80

GAC CAG GTG GAA ACT CAA GCC TGC ACT CGG GAA CAG AAC CGC ATC TGC      288
Asp Gln Val Glu Thr Gln Ala Cys Thr Arg Glu Gln Asn Arg Ile Cys
                 85                  90                  95

ACC TGC AGG CCC GGC TGG TAC TGC GCG CTG AGC AAG CAG GAG GGG TGC      336
Thr Cys Arg Pro Gly Trp Tyr Cys Ala Leu Ser Lys Gln Glu Gly Cys
             100                 105                 110

CGG CTG TGC GCG CCG CTG CGC AAG TGC CGC CCG GGC TTC GGC GTG GCC      384
Arg Leu Cys Ala Pro Leu Arg Lys Cys Arg Pro Gly Phe Gly Val Ala
         115                 120                 125

AGA CCA GGA ACT GAA ACA TCA GAC GTG GTG TGC AAG CCC TGT GCC CCG      432
Arg Pro Gly Thr Glu Thr Ser Asp Val Val Cys Lys Pro Cys Ala Pro
130                 135                 140

GGG ACG TTC TCC AAC ACG ACT TCA TCC ACG GAT ATT TGC AGG CCC CAC      480
Gly Thr Phe Ser Asn Thr Thr Ser Ser Thr Asp Ile Cys Arg Pro His
145                 150                 155                 160

CAG ATC TGT AAC GTG GTG GCC ATC CCT GGG AAT GCA AGC ATG GAT GCA      528
Gln Ile Cys Asn Val Val Ala Ile Pro Gly Asn Ala Ser Met Asp Ala
                 165                 170                 175

GTC TGC ACG TCC ACG TCC CCC ACC CGG AGT ATG GCC CCA GGG GCA GTA      576
Val Cys Thr Ser Thr Ser Pro Thr Arg Ser Met Ala Pro Gly Ala Val
             180                 185                 190

CAC TTA CCC CAG CCA GTG TCC ACA CGA TCC CAA CAC ACG CAG CCA ACT      624
His Leu Pro Gln Pro Val Ser Thr Arg Ser Gln His Thr Gln Pro Thr
         195                 200                 205

CCA GAA CCC AGC ACT GCT CCA AGC ACC TCC TTC CTG CTC CCA ATG GGC      672
Pro Glu Pro Ser Thr Ala Pro Ser Thr Ser Phe Leu Leu Pro Met Gly
210                 215                 220

CCC AGC CCC CCA GCT GAA GGG AGC ACT GGC GAC                          705
Pro Ser Pro Pro Ala Glu Gly Ser Thr Gly Asp
225                 230                 235
```

(2) INFORMATION FOR SEQ ID NO:8:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:8:

```
Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
     50                  55                  60
```

-continued

```
Trp Asn Trp Val Pro Glu Cys Leu Ser Cys Gly Ser Arg Cys Ser Ser
 65                 70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```